United States Patent
Yates et al.

(10) Patent No.: US 11,786,321 B2
(45) Date of Patent: *Oct. 17, 2023

(54) ROBOTIC SURGICAL TOOLS WITH LATCHING MECHANISM

(71) Applicant: CILAG GMBH INTERNATIONAL, Zug (CH)

(72) Inventors: David C. Yates, West Chester, OH (US); Thomas William Lytle, IV, Liberty Township, OH (US); Kharyl Evenson George Stephens, Cincinnati, OH (US); John Scott Kimsey, Walton, KY (US); Lauren S. Weaner, West Chester, OH (US); Joshua Dean Young, Loveland, OH (US)

(73) Assignee: Cilag GmbH International, Zug (CH)

( * ) Notice: Subject to any disclaimer, the term of this patent is extended or adjusted under 35 U.S.C. 154(b) by 371 days.

This patent is subject to a terminal disclaimer.

(21) Appl. No.: 17/034,827

(22) Filed: Sep. 28, 2020

(65) Prior Publication Data
US 2021/0007813 A1  Jan. 14, 2021

Related U.S. Application Data

(63) Continuation of application No. 15/823,851, filed on Nov. 28, 2017, now Pat. No. 10,786,316.

(51) Int. Cl.
*A61B 34/30* (2016.01)
*A61B 17/29* (2006.01)
*A61B 17/00* (2006.01)

(52) U.S. Cl.
CPC .............. *A61B 34/30* (2016.02); *A61B 17/29* (2013.01); *A61B 2017/00477* (2013.01); *A61B 2034/302* (2016.02); *A61B 2034/305* (2016.02)

(58) Field of Classification Search
CPC .......... A61B 34/30; A61B 2017/00477; A61B 2017/0046
See application file for complete search history.

(56) References Cited

U.S. PATENT DOCUMENTS 6,451,027 B1  9/2002  Cooper et al.
8,831,782 B2  9/2014  Itkowitz
(Continued)

FOREIGN PATENT DOCUMENTS

DE       10155734 C1   4/2003
WO       2014/151621  9/2014
WO       2014/151952  9/2014

*Primary Examiner* — Todd J Scherbel

(57) ABSTRACT

A robotic surgical system includes a robotic manipulator that includes a mounting fixture defining a longitudinal channel, and a surgical tool removably coupleable to the mounting fixture. The surgical tool including a tool housing matable with the mounting fixture, an elongate shaft extending from the tool housing and receivable within the channel, and a latching mechanism provided on the elongate shaft and comprising one or more retention tabs biased radially outward with one or more biasing members. The one or more retention tabs are movable between a deployed state, where the one or more retention tabs protrude radially outward through a corresponding one or more slots to engage the mounting fixture, and a retracted state, where the one or more retention tabs are urged radially inward through the one or more slots to disengage the mounting fixture.

7 Claims, 14 Drawing Sheets

(56) References Cited

U.S. PATENT DOCUMENTS

| | | | |
|---|---|---|---|
| 10,786,316 B2* | 9/2020 | Yates | A61B 17/29 |
| 2008/0065112 A1* | 3/2008 | Tovey | A61B 34/30 |
| | | | 606/130 |
| 2015/0073407 A1* | 3/2015 | Dickhans | A61B 1/00133 |
| | | | 606/41 |
| 2015/0313676 A1 | 11/2015 | Deodhar | |
| 2016/0287252 A1 | 10/2016 | Parihar | |
| 2018/0325500 A1* | 11/2018 | Shuart | A61B 50/13 |

* cited by examiner

ROBOTIC SURGICAL TOOLS WITH LATCHING MECHANISM

BACKGROUND

Minimally invasive surgical (MIS) tools and procedures can often be preferred over traditional open surgical techniques due to their ability to decrease post-operative recovery time and to leave minimal scarring. Laparoscopic surgery is one type of MIS procedure in which one or more small incisions are formed in the abdomen of a patient and a trocar is inserted through each incision to provide a surgical access pathway for an appropriate surgical tool. Trocars can additionally provide an internal seal assembly used for maintaining insufflation of the abdomen during a surgical procedure.

A variety of MIS tools can be inserted into the abdominal cavity of a patient via a trocar and maneuvered from outside the abdomen. Laparoscopic surgical tools, for example, are often similar to those used in traditional surgical procedures, with the exception that laparoscopic surgical tools possess an elongate shaft extending from an end effector to a location outside the abdomen. The end effector is the surgically functional part of the surgical tool. The elongate shaft protrudes externally through a trocar when the surgical tool is inserted in the abdomen of a patient, and an external portion of the surgical tool provides a means for manipulating and communicating with the end effector. Once inserted in a patient's body, the end effector can engage and/or treat tissue in a number of ways to achieve a desired diagnostic or therapeutic effect. Illustrative end effectors of laparoscopic and similar surgical tools include, but are not limited to, scissors, graspers, needle drivers, clamps, staplers, cauterizers, suction tools, irrigation tools, clip appliers, and the like.

Robotic surgery represents a specialized class of laparoscopic surgical procedures. Instead of directly engaging a surgical tool, as in traditional laparoscopic surgery, a surgeon instead manipulates and engages the surgical tool using an electronic interface communicatively coupled to a robotic manipulator. Manipulation and engagement of a surgical tool under robotic control can allow much more precise surgical procedures to be performed in many instances. In some instances, a surgeon need not even be in the operating room with the patient. Advantageously, robotic surgical systems can allow intuitive hand movements to be realized by maintaining a natural eye-hand axis. In addition, robotic surgical systems can incorporate a "wrist" coupling the end effector to the elongate shaft to provide natural, hand-like articulation during a robotic surgical procedure. The wrist can also facilitate an expanded and more complex range of motion than is possible with a human wrist, which can allow highly elaborate and precise surgical procedures to be performed.

In robotic surgery procedures and systems, a surgical tool is removably coupled via a mounting fixture (also referred to as a tool driver) to an arm of a robotic manipulator, and the surgical tool is then manipulated and engaged via the robotic manipulator under a surgeon's direction. Mounting the surgical tool to the robotic manipulator may take place using mating techniques such as, for example, snap or press fitting, slidable coupling, complementary part coupling, mechanical attachment, magnetic coupling and the like. In many instances, such mating techniques can be sufficient to hold a surgical tool in place throughout a surgical procedure.

Although these mating techniques are usually sufficient to maintain coupling to the mounting fixture, elevated tensile loads within the robotic surgical tool during use can result in inadvertent and unplanned tool decoupling from the robotic manipulator. Additional factors that may lead to unplanned tool decoupling include, for example, internal loading of the robotic surgical tool or external loading arising from biasing against a patient or another surgical tool. Rotational loading and impact loading may also occur in some instances and likewise promote unplanned tool decoupling. Unplanned tool decoupling can be hazardous to both a patient and operating room personnel, as well as potentially damaging the robotic surgical tool and/or the robotic manipulator.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
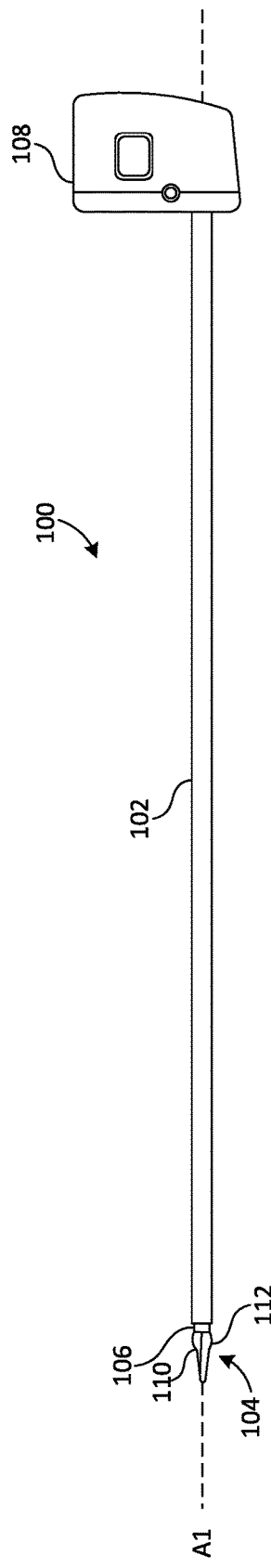
FIG. 1 shows a diagram of an illustrative robotic surgical tool that may incorporate certain principles of the present disclosure.

The present disclosure generally describes robotic surgical tools and, more specifically, systems and methods for securing a robotic surgical tool to a mounting fixture of a robotic manipulator.

As discussed above, robotic surgical tools can be subject to extreme forces, including high tensile loads, under certain circumstances during a surgical procedure. In some instances, such forces can be significant enough to promote unwanted tool decoupling from the mounting fixture of a robotic manipulator.

The present disclosure describes systems and methods that employ a latching mechanism as a secondary fastener for more robustly coupling a robotic surgical tool to the mounting fixture of a robotic manipulator. The latching mechanisms disclosed herein aid in avoiding inadvertent tool decoupling during a surgical procedure. The latching mechanisms can be deployed automatically under the influence of a biasing force once the robotic surgical tool has been coupled to the mounting fixture.

At least some configurations of the latching mechanisms disclosed herein can perform an additional function of engaging cables or similar elongate members that are used for operating the end effector of the robotic surgical tool. In particularly advantageous configurations, cable engagement may occur when the latching mechanism is non-deployed, such as when loading or unloading the robotic surgical tool from the mounting fixture, as discussed in further detail herein. Cable engagement may lock the cables into place in this configuration, which can advantageously prevent unwanted movement of the end effector, except when desired during a surgical procedure. In other suitable configurations, cable engagement may occur when the latching mechanism is deployed, which may aid in maintaining the cables in a tensioned state to promote accurate articulation of the end effector during a robotic surgical procedure.

Before discussing the latching mechanisms of the present disclosure, a brief overview of robotic surgical tools and robotic surgical systems will be provided hereinafter in order for the embodiments of the present disclosure to be better understood. Many of the concepts and features discussed hereinafter are also applicable to the tools, systems and methods described in the present disclosure, as will be appreciated by one having ordinary skill in the art.

The terms "proximal" and "distal" are defined herein relative to the location of tool engagement by a robotic manipulator. The term "proximal" refers to a position closer to the location of tool engagement with the robotic manipulator (i.e., further away from a patient), and the term "distal" refers to a position more removed from the location of tool engagement with the robotic manipulator (i.e., nearer to a patient). Moreover, directional terms such as above, below, upper, lower, upward, downward, left, right, and the like are used to describe relative position in the figures and thus should not be considered limiting.

FIG. 1 shows a diagram of an illustrative robotic surgical tool 100 that may incorporate certain principles of the present disclosure. Robotic surgical tool 100 includes elongate shaft 102, end effector 104 located at a distal end of elongate shaft 102, and tool housing 108 located at a proximal end of elongate shaft 102. Wrist 106 is also located at a distal end of elongate shaft 102 and couples end effector 104 thereto. Tool housing 108 is configured for releasable coupling with a mounting fixture of a robotic manipulator (see FIGS. 6-11), alternately referred to as a "robot" or "surgical robot." Tool housing 108 contains various mechanisms (obscured in FIG. 1) which may be actuated through a mechanical interface with the surgical robot to produce one or more resultant motions in end effector 104. A surgeon may interface with the surgical robot to control the various actuations occurring in tool housing 108 and thereby direct operation of end effector 104. More particularly, actuation within tool housing 108 controls operation of end effector 104 via retraction and extension of cables or similar elongate members (obscured in FIG. 1) that are operably engaged with end effector 104.

Tool housing 108 may be releasably coupled with the mounting fixture of a robotic manipulator in a variety of ways, such as by clamping or clipping thereto, or slidably mating therewith. Illustrative mechanisms for releasably coupling tool housing 108 to a mounting fixture are described in more detail in U.S. Patent Application Publications 2015/0209965, 2015/0025549 and 2017/0252096, which are incorporated herein by reference in their entirety Illustrative robotic surgical systems are also described in these references as well as in U.S. Pat. No. 8,831,782, which is also incorporated herein by reference in its entirety.

Continuing with FIG. 1, end effector 104 is configured to move relative to elongate shaft 102 at wrist 106, such as by pivoting at wrist 106, to position end effector 104 at a desired orientation and location relative to a surgical site during a surgical procedure. Tool housing 108 includes various components designed to position and operate various features of end effector 104 (e.g., one or more of clamping, cutting, firing, rotation, articulation, energy delivery, and the like). In illustrative embodiments, one or more elongate members can extend from tool housing 108 through wrist 106 to facilitate movement of end effector 104, as discussed in more detail hereinbelow. In at least some embodiments, elongate shaft 102 and end effector 104 coupled distally thereto are configured to rotate about longitudinal axis A1. In some embodiments, various components of tool housing 108 can be configured to facilitate rotational motion of elongate shaft 102 and end effector 104 about longitudinal axis A1. In other embodiments, elongate shaft 102 may be fixed to tool housing 108, in which case robotic surgical tool 100 may be rotated by the robotic manipulator to reposition elongate shaft 102 and end effector 104.

Robotic surgical tool 100, particularly at end effector 104, can be configured to perform at least one surgical function. The choice of end effector 104 can determine which surgical function robotic surgical tool 100 is able to perform. Illustrative configurations of end effector 104 that may be present in robotic surgical tool 100 include, for example, forceps, graspers, needle drivers, scissors, electrocauterization tools that apply energy to tissue, staplers, clip appliers, suctioning tools, hooks, spatulas, irrigation tools, imaging devices (e.g., endoscopes or ultrasonic probes), and any combination thereof. In at least one embodiment, robotic surgical tool 100 may be configured to apply mechanical force to a tissue. The mechanical force can be conveyed to end effector 104 via the cables or similar elongate members extending through elongate shaft 102.

Elongate shaft 102 extends distally from tool housing 108 and has at least one lumen (see FIG. 3) extending internally therethrough. Elongate shaft 102 may be affixed to tool housing 108, but alternately may be releasably coupled so as to be interchangeable with other types of elongate shafts, such as elongate shafts have a differing diameter. In at least some embodiments, elongate shaft 102 may be rotatably coupled to tool housing 108.

End effector 104 can have a variety of sizes, shapes and configurations. In the illustrative configuration of FIG. 1, end effector 104 comprises a tissue grasper or needle driver having opposing jaws 110 and 112 that are configured to move (pivot) between open and closed positions. In addition, the entirety of end effector 104 may pivot relative to elongate shaft 102 at wrist 106. Pivoting may place end effector 104 in a better position to engage tissue during a surgical procedure. Other suitable configurations for end effector 104 include, but are not limited to, scissors including a pair of opposed cutting jaws, babcocks including a pair of opposed grasping jaws, retractors, and the like. Additional configurations suitable for end effector 104 are also provided hereinabove.

Wrist 106 can likewise have a variety of configurations. In the illustrative configuration of FIG. 1, wrist 106 includes a joint configured to allow movement of end effector 104 relative to elongate shaft 102, such as a pivot joint at which jaws 110 and 112 are pivotally attached. Illustrative configurations that may be similar to wrist 106 and are suitable for use in the embodiments of the present disclosure include those described in U.S. Patent Application Publications 2015/0209965, 2015/0025549 and 2017/0252096, each previously incorporated by reference above.

Figure 2:
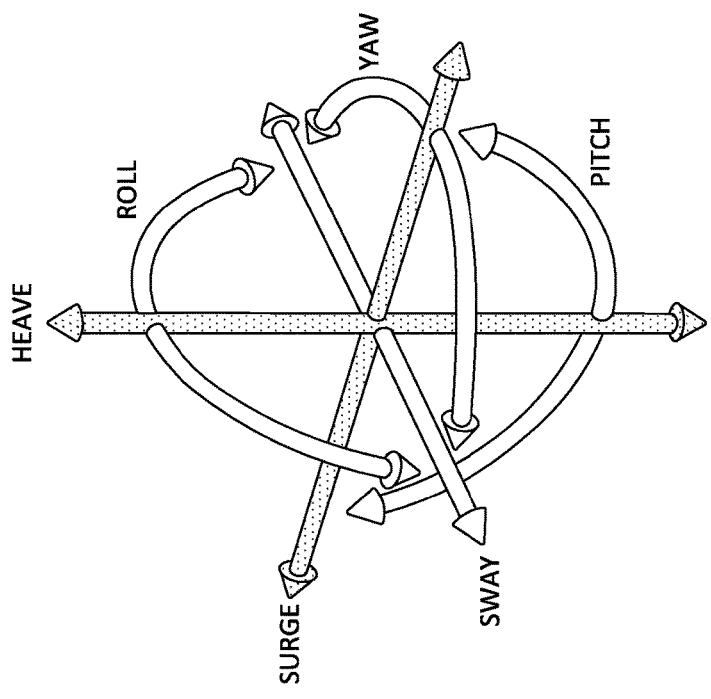
FIG. 2 shows a diagram illustrating the degrees of freedom through which a wrist of a robotic surgical tool may articulate.

FIG. 2 shows a diagram illustrating the degrees of freedom through which wrist 106 may articulate. More specifically, the degrees of freedom available to wrist 106 are represented by three translational or position variables (e.g., surge, heave and sway) and three rotational or orientation variables (e.g., Euler angles or roll, pitch and yaw). The translational and rotational variables collectively describe the position and orientation of one or more components of a surgical system (e.g., wrist 106 and associated end effector 104) with respect to a given frame of reference, such as a Cartesian coordinate system or spherical coordinate system. As illustrated in FIG. 2, the term "surge" refers to forward and backward movement, the term "heave" refers to up and down movement, and the term "sway" refers to left and right movement. With regard to the rotational terms in FIG. 2, "roll" refers to side-to-side tilting, "pitch" refers to forward and backward tilting, and "yaw" refers to left and right turning.

In some embodiments, a pivoting motion can include pitch movement about a first axis of wrist 106 (e.g., X-axis), yaw movement about a second axis of wrist 106 (e.g., Y-axis), and combinations thereof to allow for 360° rotational movement of end effector 104 about wrist 106. In other embodiments, a pivoting motion can be limited to movement in a single plane such that end effector 104 rotates only in a single plane (e.g., only pitch movement about a first axis of wrist 106 or only yaw movement about a second axis of wrist 106).

Figure 3:
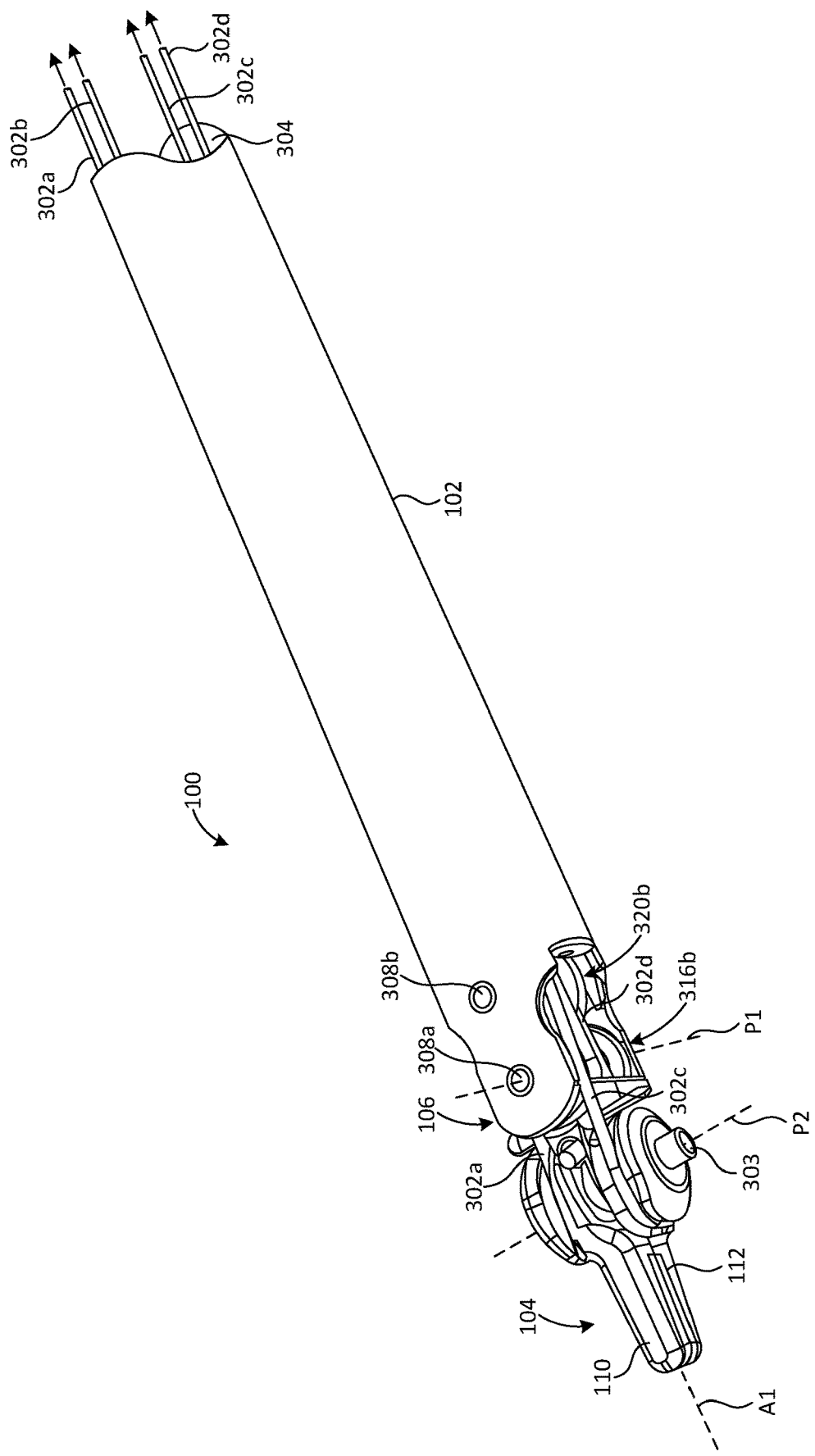
FIGS. 3-5 show various views of an illustrative robotic surgical tool containing an end effector.
Figure 4:
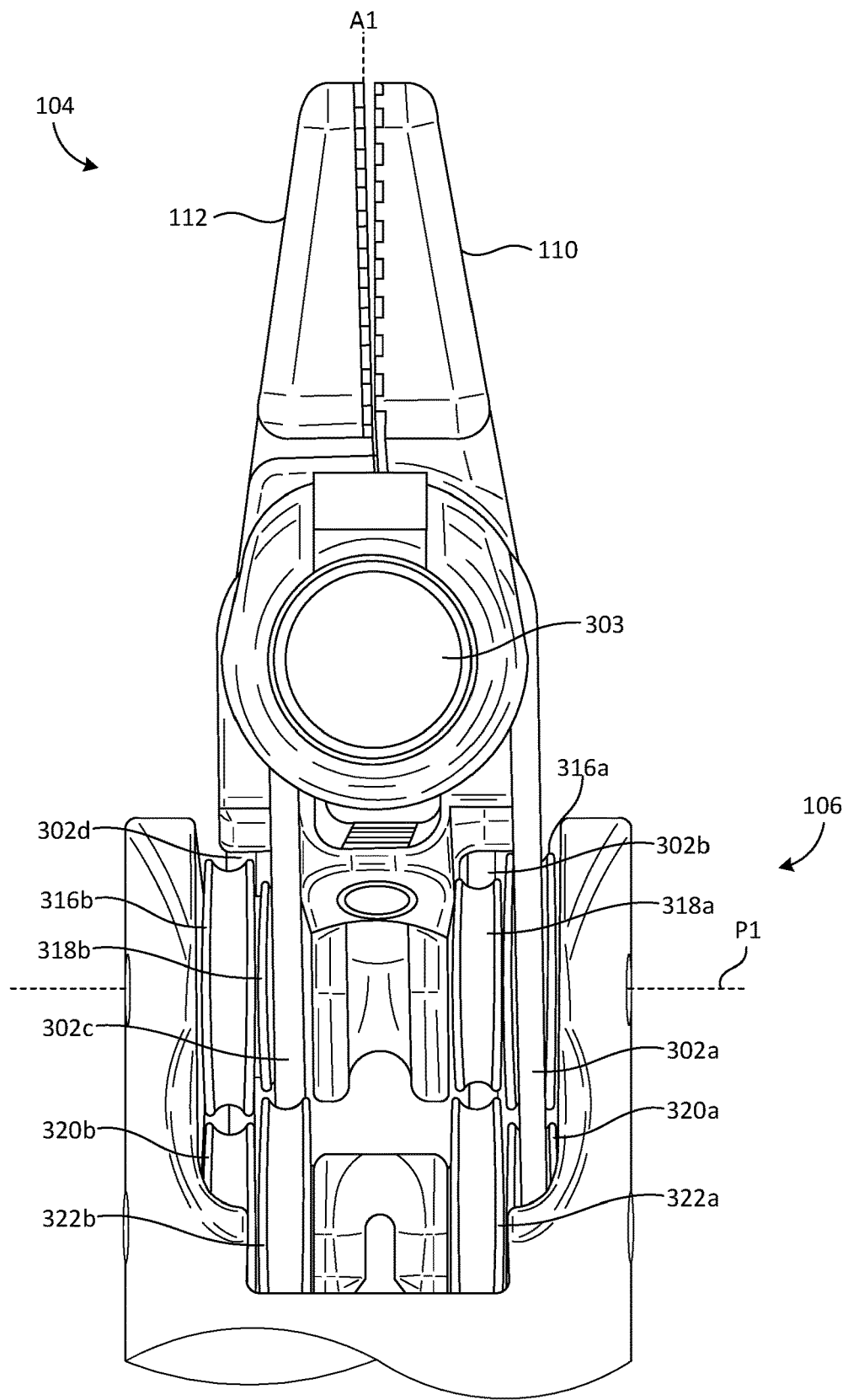
Figure 5:
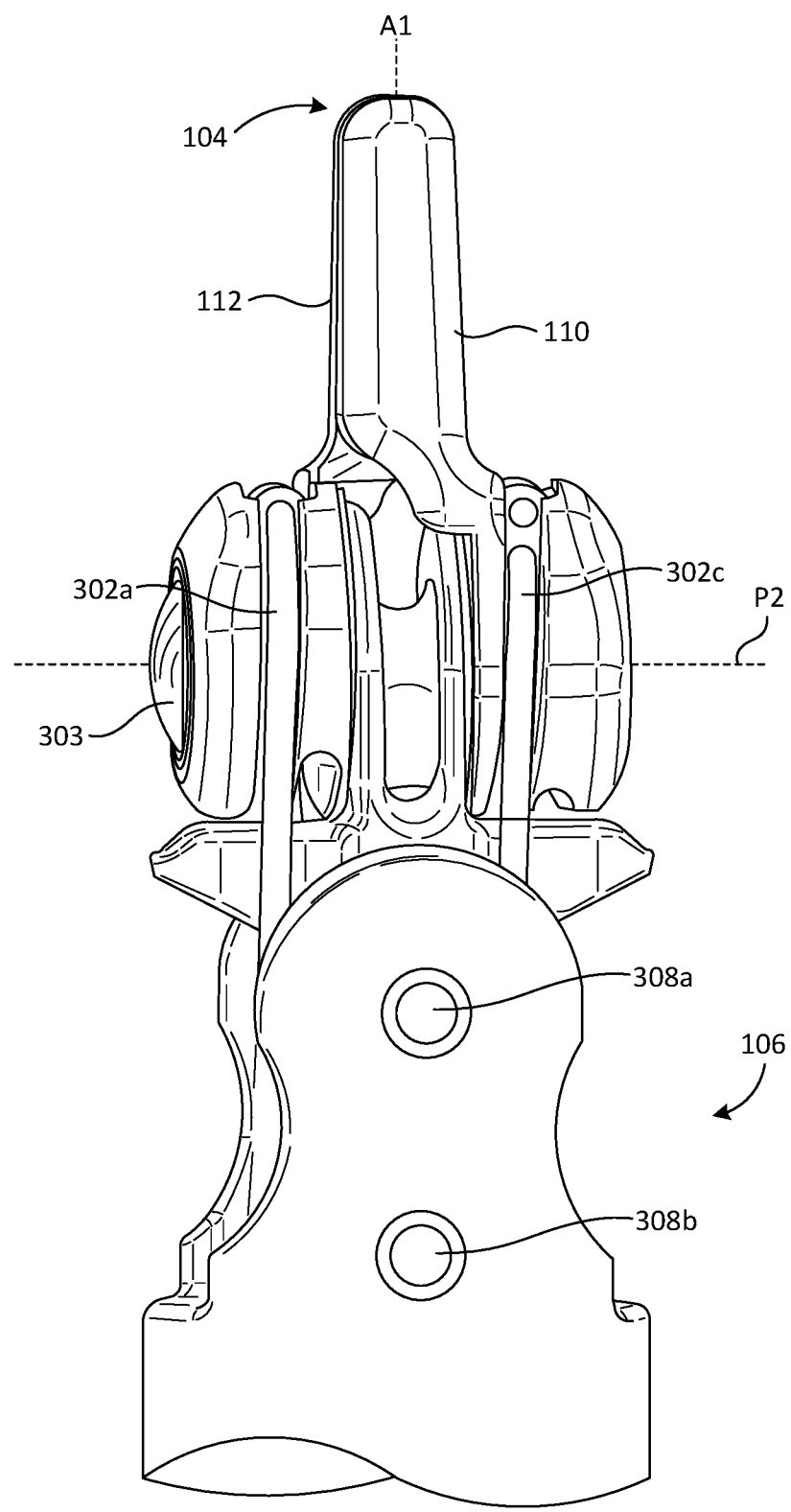

FIGS. 3-5 show enlarged views of the distal end of robotic surgical tool 100. As illustrated, robotic surgical tool 100 includes a plurality of cables or similar elongate members (referred to as "cables" hereinafter), which are depicted as elongate members 302a, 302b, 302c, and 302d within lumen 304. Elongate members 302a-d further extend into tool housing 108 (not shown in FIGS. 3-5) and are configured to impart movement to end effector 104 relative to elongate shaft 102. Illustrative forms of the elongate members 302a-d include, for example, cables, bands, lines, cords, wires, ropes, strings, twisted strings and the like. Elongate members 302a-d can be formed from any of a variety of high-durability materials, such as a metal (e.g., tungsten, stainless steel, and like materials) or a polymer. In at least one embodiment, one or more of the elongate members 302a-d may be made of a flexible material. Illustrative cables and similar elongate members are described in U.S. Patent Application Publications 2015/0209965 and 2015/0025549, each previously incorporated herein by reference.

Although robotic surgical tool 100 is depicted in FIGS. 3-5 as including four elongate members 302a-d, one pair being operatively coupled to each of jaws 110 and 112, alternative configurations can have differing numbers of elongate members. For example, a robotic surgical tool having an end effector that does not require internal motion can include two elongate members configured to provide articulation upon longitudinal tensioning and de-tensioning.

Elongate members 302a-d extend longitudinally within lumen 304 of elongate shaft 102 through wrist 106 and operably engage end effector 104, as described hereinafter. The proximal ends of elongate members 302a-d are similarly operably engaged with components in tool housing 108 (not shown in FIG. 3). The components in tool housing 108 are, in turn, configured for actuation by one or more drive inputs received from a surgical robot. One or more of elongate members 302a-d may be selectively translated longitudinally to cause end effector 104 to move (e.g., pivot in one or more locations) relative to elongate shaft 102. Depending on the required motion, one or more of elongate members 302a-d may translate longitudinally to articulate end effector 104 (e.g., to move jaws 110 and 112 at an angle in a same direction), to open end effector 104 (e.g., to move jaws 110 and 112 away from one another), to close end effector 104 (e.g., to move jaws 110 and 112 toward one other), or any combination thereof.

Although a single lumen 304 is depicted in FIG. 3, multiple lumens can be present in alternative embodiments, such that one or more of elongate members 302a-d is housed within each of the multiple lumens. In further alternative embodiments, one or more of elongate members 302a-d can extend along the exterior of elongate shaft 102, such as in longitudinal channels formed in an exterior surface of elongate shaft 102.

Referring still to FIG. 3, and with further reference to FIGS. 4 and 5, wrist 106 includes multiple pulleys for engaging and redirecting elongate members 302a-d during their longitudinal translation. Specifically, wrist 106 includes distal plurality of pulleys 316a, 316b, 318a and 318b, and proximal plurality of pulleys 320a, 320b, 322a and 322b. A small gap (best shown in FIG. 4) is defined between corresponding pulleys in the distal and proximal pluralities of pulleys, which is sized for passage of elongate members 302a-d therethrough. Pulleys 316a, 316b, 318a and 318b are mounted to distal wrist axle 308a, and pulleys 320a, 320b, 322a and 322b are mounted to proximal wrist axle 308b. End effector 104 is operably coupled to wrist 106 such that distal wrist axle 308a defines first pivot axis P1 during operation thereof.

Robotic surgical tool 100 further includes second pivot axis P2 along end effector axle 303, about which jaws 110 and 112 of end effector 104 are configured to pivot relative to each other (in tandem or separately) between extremes of open and closed positions, and/or about which jaws 110 and 112 are configured to move together during articulation of end effector 104. As illustrated, second pivot axis P2 is substantially perpendicular to longitudinal axis A1. A person having ordinary skill in the art will appreciate that axes A1 and P2 may not be precisely perpendicular to one another but nevertheless be considered to be substantially perpendicular due to any number of factors, such as manufacturing tolerance and precision of measurement devices.

Robotic surgical tool 100 has two joints at second pivot axis P2, one joint for each of jaws 110 and 112. Actuation of at least one of elongate members 302a-d causes movement of jaw 110 and/or jaw 112 at the associated joint(s) along second pivot axis P2. In an exemplary embodiment, jaws 110 and 112 are configured to pivot in tandem at their associated joints. That is, during opening of jaws 110 and 112, each of jaws 110 and 112 rotates at its associated joint, and during closing of jaws 110 and 112, each of jaws 110 and 112 rotates in the opposite direction at its associated joint.

Figure 6:
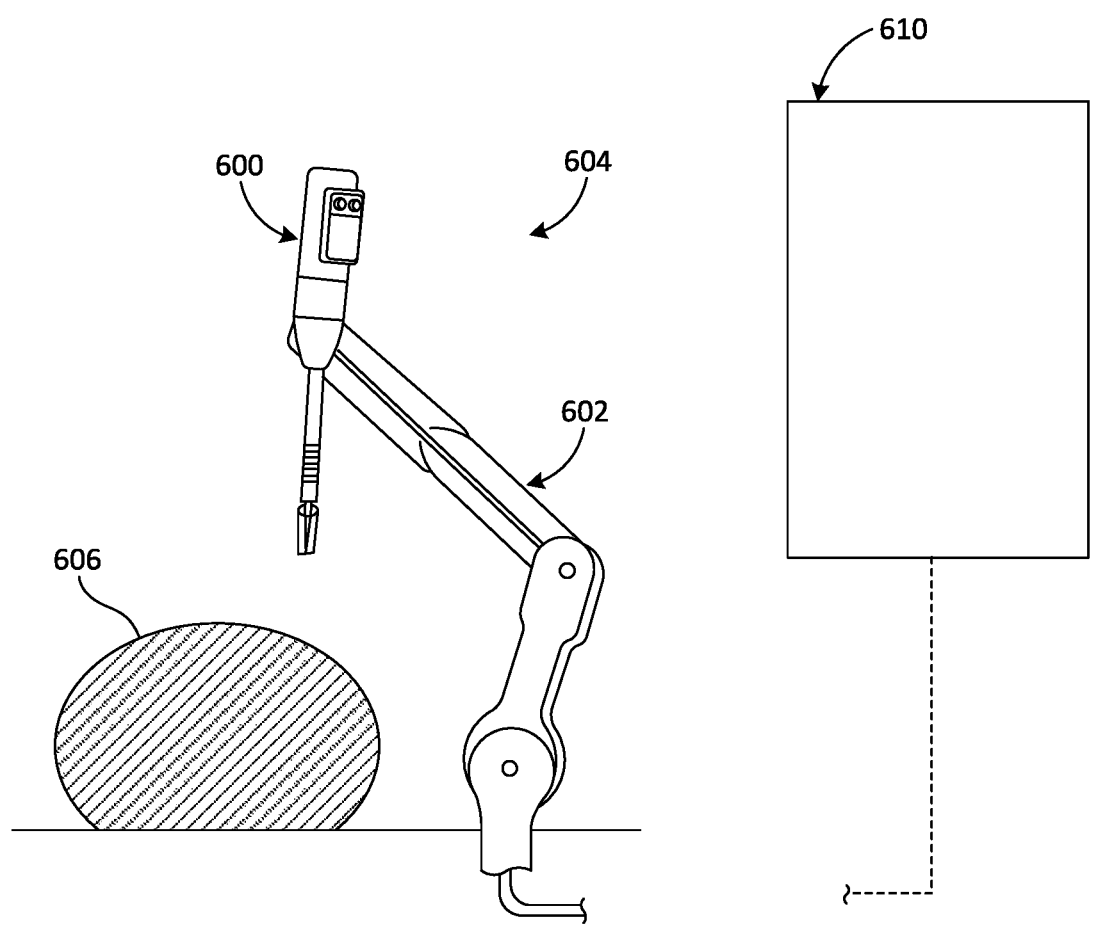
FIG. 6 shows a diagram of an illustrative manner of coupling between a robotic surgical tool and a robotic manipulator.

Robotic surgical tool 100 is configured for releasable coupling to a robotic manipulator. FIG. 6 shows a diagram of an illustrative manner of coupling between a robotic surgical tool and a robotic manipulator. It is to be understood that the manner of coupling depicted in FIG. 6 is illustrative in nature only so that the embodiments of the present disclosure can be better understood. In non-limiting variations, the type of robotic surgical tool and/or robotic manipulator, and/or the manner of coupling, for example, may differ based upon considerations that will be familiar to one having ordinary skill in the art. As depicted in FIG. 6, robotic surgical tool 600 is coupled to arm 602 of robotic manipulator 604. Robotic manipulator 604 and robotic surgical tool 600 releasably coupled thereto are positioned adjacent to patient 606 in order to conduct a surgical procedure thereon. Robotic manipulator 604 is in electronic communication with control system 610, through which a surgeon may move arm 602 and/or actuate robotic surgical tool 600 according to one or more embodiments. Although FIG. 6 has depicted a wired connection between robotic surgical tool 600 and control system 610, wireless configurations also reside within the scope of the present disclosure. In one or more embodiments, control system 610 may include vision control, processing control, or any combination thereof, using any combination of software and hardware processing.

Figure 7:
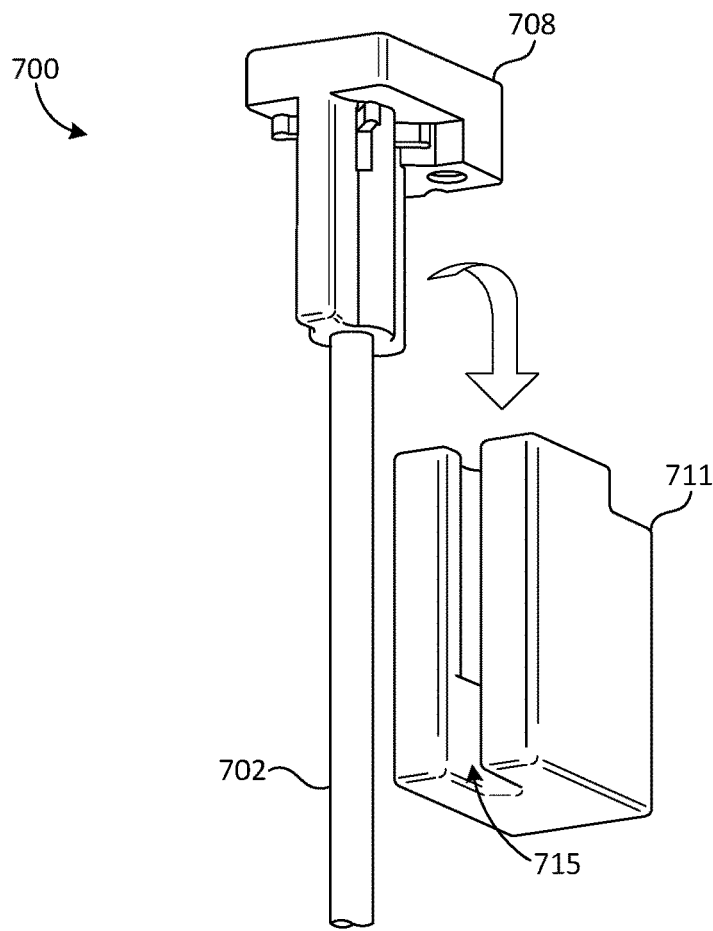
FIGS. 7 and 8 show diagrams illustrating more details of the releasable coupling between a robotic surgical tool and a mounting fixture of a robotic manipulator, which may incorporate certain principles of the present disclosure.
Figure 8:
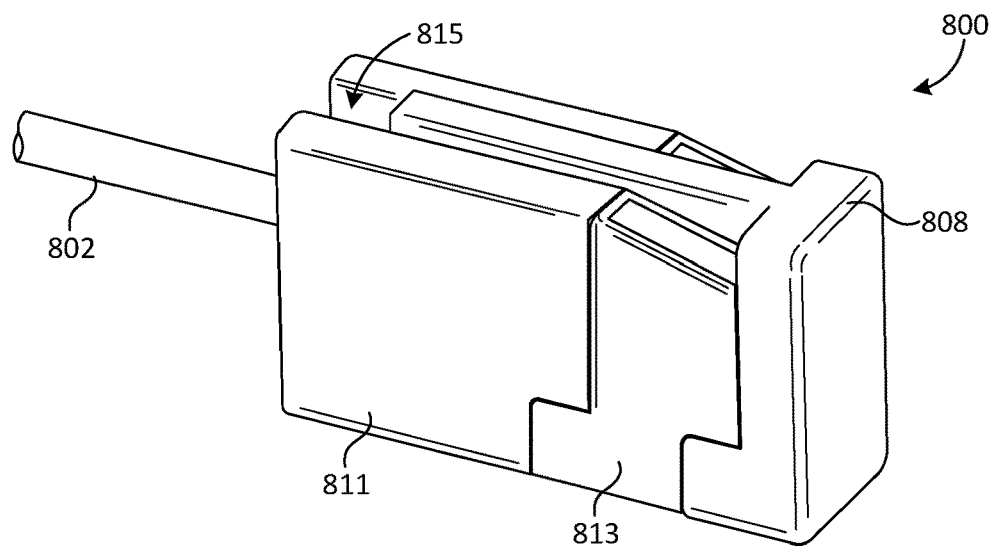

FIGS. 7 and 8 show diagrams illustrating more details of the releasable coupling between a robotic surgical tool and a mounting fixture of a robotic manipulator, which may incorporate certain principles of the present disclosure. FIG. 7 shows robotic surgical tool 700 and mounting fixture 711 (remainder of the robotic manipulator not shown) prior to coupling therebetween. Robotic surgical tool 700 is similar in many respects to robotic surgical tool 100 and may be better understood by reference to FIGS. 1 and 3-5 and their accompanying description. Similar to robotic surgical tool 100, robotic surgical tool 700 likewise includes elongate shaft 702 and tool housing 708. Mounting fixture 711 includes channel 715, which is sized to receive elongate shaft 702. Interior motors (not shown in FIG. 7) within mounting fixture 711 allow an end effector coupled to elongate shaft 702 to be actuated. Elongate shaft 702 may pass through channel 715 when releasably coupling tool housing 708 to mounting fixture 711 in the course of readying robotic surgical tool 700 for a surgical procedure. Although FIG. 7 has depicted channel 715 as being hemispherical or similarly open-faced (i.e., open on one longitudinal side), closed-face (i.e., fully enclosed or tube-like) mounting fixture configurations are also within the scope of the present disclosure.

A sterile barrier may be interposed between a robotic surgical tool and a mounting fixture of a robotic manipulator, as shown in FIG. 8. FIG. 8 shows tool housing 808 of robotic surgical tool 800 coupled to mounting fixture 811 with sterile barrier 813 interposed in between. Robotic surgical tool 800 is similar in many respects to robotic surgical tools 100 and 700 and may be better understood by making further reference to FIGS. 1, 3-5 and 7 and their accompanying description. Elongate shaft 802 similarly passes through channel 815 of mounting fixture 811 once tool housing 808 is coupled to mounting fixture 811 via sterile barrier 813. Sterile barrier 813 may aid in maintaining a sterile surgical field during use of robotic surgical tool 800. Surgical drapes, shrouds or similar barrier-like structures may be present as integral components of sterile barrier 813 and further aid in maintaining a sterile surgical field in the vicinity of mounting fixture 811. Illustrative sterile barriers having an incorporated sterile drape, for example, are described in U.S. Pat. No. 8,220,468, which is incorporated herein by reference.

As indicated previously, robotic surgical tools, such as those discussed hereinabove, may be susceptible to decoupling from the mounting fixture of a robotic manipulator and/or a sterile barrier under certain excessive force conditions, such as excessive tensile loads, impact loads, internal or external loading, rotational loading, and biasing forces. Upwardly directed forces in excess of a certain magnitude may particularly promote decoupling of a robotic surgical tool from its mounting fixture by overcoming the releasable coupling force otherwise holding the tool and the mounting fixture together. As used herein, the term "upwardly directed force" refers to a directed force that tends to urge a robotic surgical tool out of the channel within a robotic manipulator. That is, a sufficiently strong upwardly directed force may push the robotic surgical tool longitudinally off the mounting fixture. Tensile loads assumed by the elongate members within the robotic surgical tool may approach 120 pounds of force during use and provide a sufficient upwardly directed force to promote tool decoupling. Biasing against a patient or another surface or impact loads of sufficient force may similarly promote unplanned tool decoupling.

Robotic surgical tools according to the present disclosure further include a latching mechanism that can provide a secondary coupling mechanism to supplement the coupling force ordinarily present when releasably coupling a tool housing to a mounting fixture and/or a sterile barrier. The latching mechanisms disclosed herein may be particularly adapted to resist upwardly directed forces, such as excessive tensile loads, that may otherwise promote tool decoupling. Advantageously, the latching mechanisms of the present disclosure are compatible with conventional techniques for releasably coupling a robotic surgical tool to a mounting fixture, such as those discussed hereinabove. As such, the latching mechanisms may provide compatibility with existing equipment and are not necessarily intended to replace conventional tool coupling approaches.

More specifically, the latching mechanisms may be located upon or within the elongate shaft of the robotic surgical tools and contain one or more biased retention tabs that are radially movable with respect to the elongate shaft between retracted (stowed) and deployed states. As discussed herein, the retention tabs may be in the retracted state at least at some point prior to coupling the robotic surgical tool to the mounting fixture of a robotic manipulator and then deploy radially under the influence of a biasing force in the course of tool coupling once the robotic surgical tool has been properly seated in the mounting fixture. Once the retention tabs are deployed and engage an exterior surface of the mounting fixture, such as on the underside of the mounting fixture, the robotic surgical tool cannot be withdrawn therefrom until the retention tabs are subsequently retracted. Retraction of the retention tabs may occur, either manually or using an appropriate tool, once removal of the robotic surgical tool is desired.

Some configurations of the latching mechanisms described herein may promote engagement with the cables or similar elongate members extending within the elongate shaft of the robotic surgical tool. In particular configurations, a component of latching mechanisms may be adapted to engage the cables when the retention tabs are retracted and to disengage from the cables when the retention tabs are deployed. In especially advantageous configurations, cable engagement with a component of the latching mechanisms may lock the cables in place when inserting or removing the robotic surgical tool from the mounting fixture. Cable locking during insertion and removal of the robotic surgical tool can be desirable to prevent unwanted articulation of the end effector or other tool components. Cable engagement may also occur such that the cables are tensioned without rigorously locking the cables into place. Secondary calibration of the cable tension may also take place at this juncture. In other advantageous configurations, the latching mechanisms may be configured to engage one or more of the cables when the retention tabs are deployed and the robotic surgical tool is secured in place within a mounting fixture. Cable engagement that takes place when the robotic surgical tool is secured in a mounting fixture may advantageously place a tensile load on the cables to promote accurate articulation of an end effector.

Figure 9:
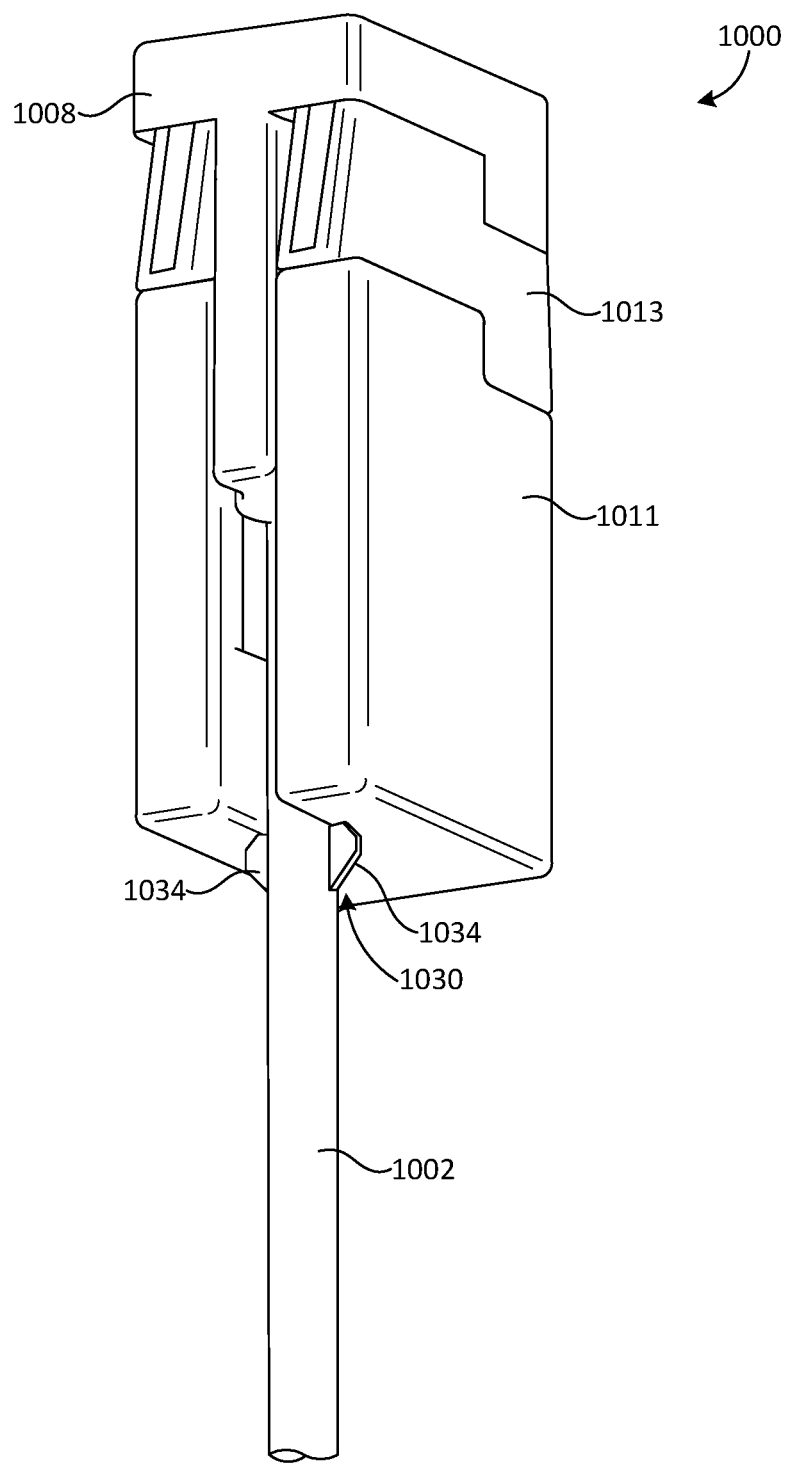
FIG. 9 shows a diagram of a first latching mechanism configuration of the present disclosure in engagement with a mounting fixture of a robotic manipulator.

FIG. 9 shows a diagram of a robotic surgical tool coupled to a mounting fixture of a robotic manipulator, where the robotic surgical tool includes a first configuration of a latching mechanism of the present disclosure. As shown in FIG. 9, housing 1008 of robotic surgical tool 1000 is removably coupled to mounting fixture 1011 via sterile barrier 1013. Although FIG. 9 has shown a tool configuration similar to that of FIG. 8, it is to be recognized that a tool configuration similar to FIG. 7 may be employed similarly without departing from the principles of the present disclosure.

Latching mechanism 1030 includes retention tabs 1034. As discussed in further detail herein, retention tabs 1034 are configured for radial deployment under the influence of an internal radial biasing force. In latching mechanism 1030, retention tabs 1034 extend directly from elongate shaft 1002 when deployed under influence of the biasing force and are housed within elongate shaft 1002 when non-deployed (stowed or retracted). Retention tabs 1034 may engage an exterior surface of mounting fixture 1011 according to one or more embodiments of the present disclosure to aid in preventing tool decoupling, as discussed in further detail herein.

Figure 10:
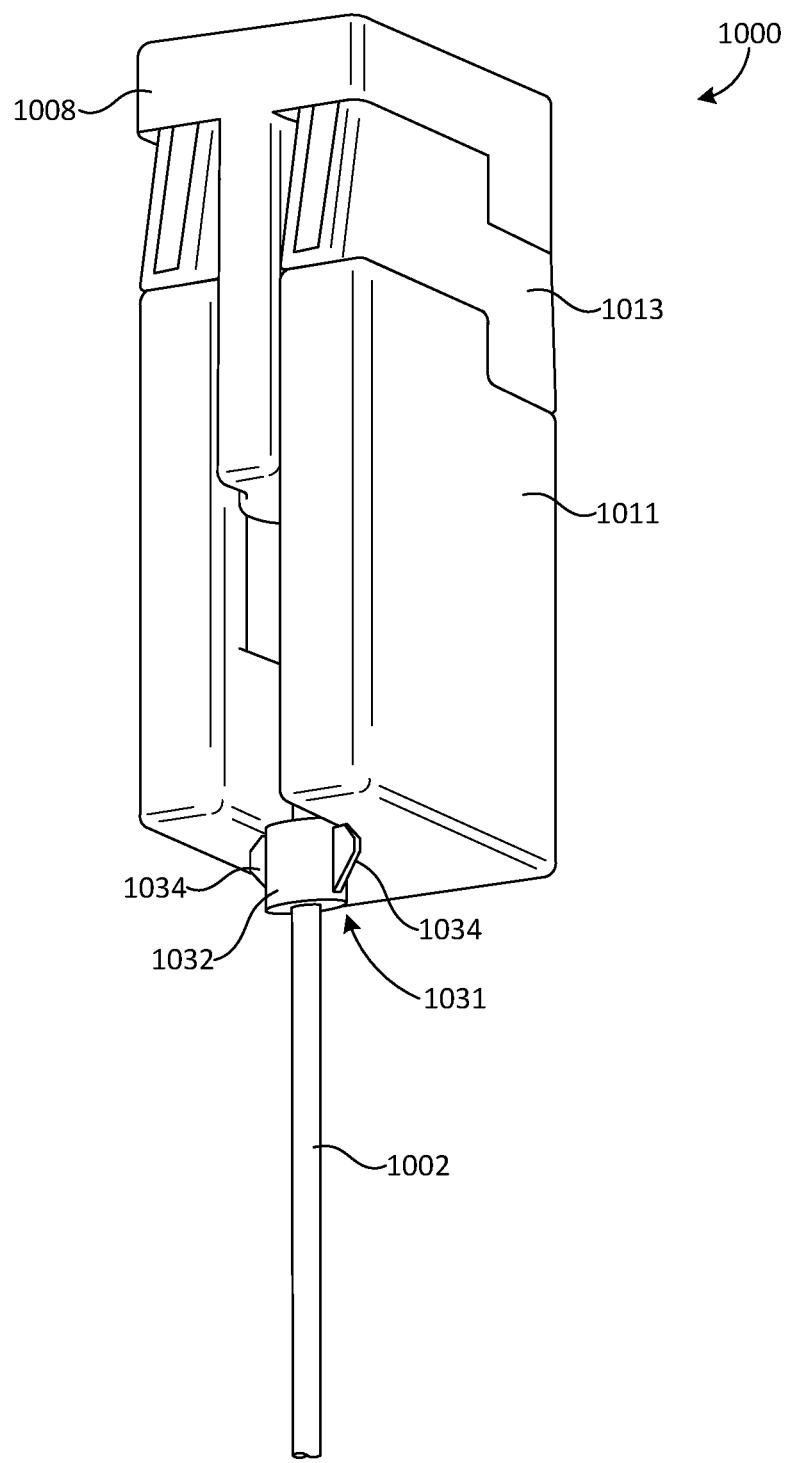
FIG. 10 shows a diagram of a second latching mechanism configuration of the present disclosure in engagement with a mounting fixture of a robotic manipulator.

FIG. 10 shows a diagram of a robotic surgical tool coupled to a mounting fixture, where the robotic surgical tool includes a second configuration of a latching mechanism of the present disclosure. FIG. 10 differs from FIG. 9 primarily in the latching mechanism configuration, and common reference characters are used to annotate and describe elements otherwise having similar structure and function. Again, although FIG. 10 has shown a tool configuration similar to that of FIG. 8, it is to be recognized that a tool configuration similar to FIG. 7 may be employed similarly without departing from the principles of the present disclosure.

Robotic surgical tool 1000 in FIG. 10 contains latching mechanism 1031, in which retention tabs 1034 extend radially from latch body 1032, rather than directly from elongate shaft 1002, as in FIG. 9. Latching mechanism 1031 and its associated latch body 1032 may provide certain advantages compared to latching mechanism 1030. Specifically, latch body 1032 may provide additional space for mechanical components such as, for example, pulleys, springs, latches and the like. As depicted, latch body 1032 is in the form of a sleeve, collar or similar structure, and it is to be understood that latch body 1032 is not necessarily drawn to scale. Latch body 1032 is fixedly coupled to the exterior of elongate shaft 1002. In general, latch body 1032 may be sized such that it can still pass through mounting fixture 1011, in a manner similar to that described above, after which retention tabs 1034 may then deploy. FIG. 10 likewise shows retention tabs 1034 engaging an exterior surface of mounting fixture 1011 to aid in preventing tool decoupling or rocking during use.

Latch body 1032 may be fixedly coupled to elongate shaft 1002 using any suitable technique. Suitable techniques for fixedly coupling latch body 1032 to elongate shaft 1002 include, but are not limited to, welding, brazing, soldering, adhesive bonding, mechanical fastening, laser welding, interference fitting, and the like. In some embodiments, latch body 1032 may be fabricated integrally with elongate shaft 1002. That is, in such embodiments, elongate shaft 1002 and latch body 1032 may define a one-piece construct instead of being fabricated from two separate pieces. Additional details directed to latch body 1032 and the disposition of retention tabs 1034 therein are provided hereinbelow.

Although FIGS. 8 and 9, have shown latching mechanisms 1030 and 1031 as containing two retention tabs 1034, it is to be recognized the differing numbers of retention tabs 1034 may be present in alternative embodiments. In general, latching mechanisms 1030 and 1031 may contain one or more retention tabs 1034. For example, in various embodiments, between one and about ten or between two and about four retention tabs may be present in either latching mechanism 1030 or latching mechanism 1031. Considerations as to how many retention tabs 1034 and related elements to include in a particular configurations reside within the purview of a person having ordinary skill in the art.

Similarly, in some embodiments, one or more biasing members may extend between two opposing retention tabs (i.e., a first retention tab and a second retention tab). In other embodiments, each retention tab may be separately biased by a single biasing member.

Figure 11:
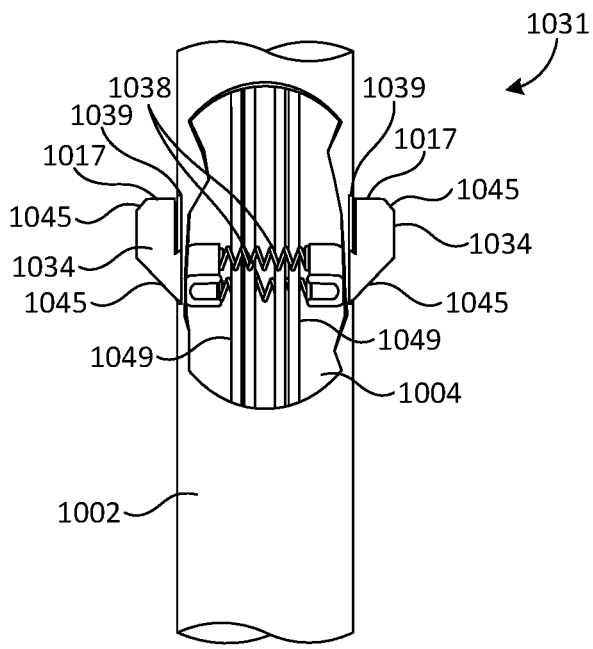
FIGS. 11 and 12 show diagrams illustrating further details of a first latching mechanism configuration, in which retention tabs are in a deployed state and a non-deployed state, respectively.
Figure 12:
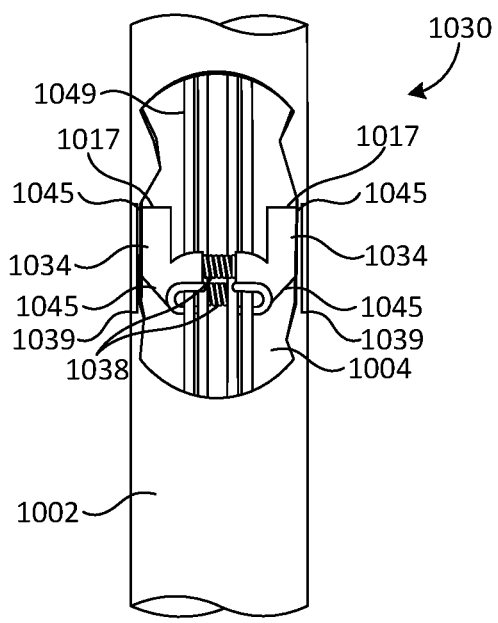

FIGS. 11 and 12 show diagrams illustrating further details of latching mechanism 1030, in which retention tabs 1034 are in a deployed state and a retracted (stowed) state, respectively. As shown, retention tabs 1034 are biased radially outward with one or more biasing members 1038 located within lumen 1004 of elongate shaft 1002. In some embodiments, biasing members 1038 may also operably couple retention tabs 1034 together such that movement of one retention tab 1034 places a radial biasing load on the other retention tab 1034.

Biasing members 1038 may be configured to autonomously deploy retention tabs 1034 at a desired time, unless the supplied biasing force is overcome to preclude deployment. Although compression springs have been shown in FIGS. 11 and 12 as illustrative biasing members 1038, it is to be understood that other types of biasing devices capable of deploying retention tabs 1034 may be employed similarly. For example, in alternative embodiments, a hydraulic or pneumatic piston, or a series of Belleville washers may be suitable for use as biasing member 1038. Other suitable biasing members 1038 may include, for example, leaf springs, magnets or electromagnets, and a vertically inserted wedge. In still other alternative embodiments, spring-loaded cams may be suitable biasing members for supplying an outward radial biasing force (see FIGS. 15 and 16).

In general, retention tabs 1034 include at least one flat (planar) surface 1017 configured for engaging a corresponding flat surface upon the exterior of mounting fixture 1011, such as the bottom surface of mounting fixture 1011, when deployed. Otherwise, the shape of retention tabs 1034 is not considered to be particularly limited. As depicted, retention tabs 1034 may also have one or more angled edges 1045 to facilitate retraction thereof. Angled edges 1045 may also afford reduced-friction engagement with a complementary mating component, such as a retraction tool, for example, as discussed below.

In the depicted configuration, elongate shaft 1002 includes slots 1039 located on an outer diameter thereof, through which retention tabs 1034 may deploy and retract from lumen 1004. As depicted in FIG. 11, the biasing force (i.e., the spring force or other similar opposing force) supplied by each biasing member 1038 is sufficient to at least partially extend retention tabs 1034 from each slot 1039. Deployment of retention tabs 1034 can occur autonomously when the exterior space proximal to slots 1039 is unoccupied, such as after latching mechanism 1030 clears mounting fixture 1011 in the course of tool coupling.

In contrast, in FIG. 12, retention tabs 1034 are stowed interiorly within lumen 1004, such as after overcoming the biasing force to ready robotic surgical tool 1000 for removal from mounting fixture 1011. Any suitable technique can be used to overcome the biasing force for retracting retention tabs 1034 interiorly. In some embodiments, a user can retract retention tabs 1034 within lumen 1004 simply by squeezing with using one's fingers. In alternative embodiments, a specialized tool can promote inward retraction of retention tabs 1034 (see FIGS. 21 and 22). In some embodiments, a human can directly supply the necessary force for overcoming the biasing force. In other embodiments, a machine, such as a surgical robot, can be operated by a user to supply the necessary force for overcoming the biasing force. The interior of mounting fixture 1011 may also maintain retention tabs 1034 in a retracted state, according to some embodiments.

As depicted in FIGS. 11 and 12, no engagement occurs between cables 1049 and retention tabs 1034 or any component thereof. As shown in subsequent FIGS., and described hereinbelow, engagement of cables 1049 many occur in other various configurations when retention tabs 1034 are retracted or deployed.

Figure 13:
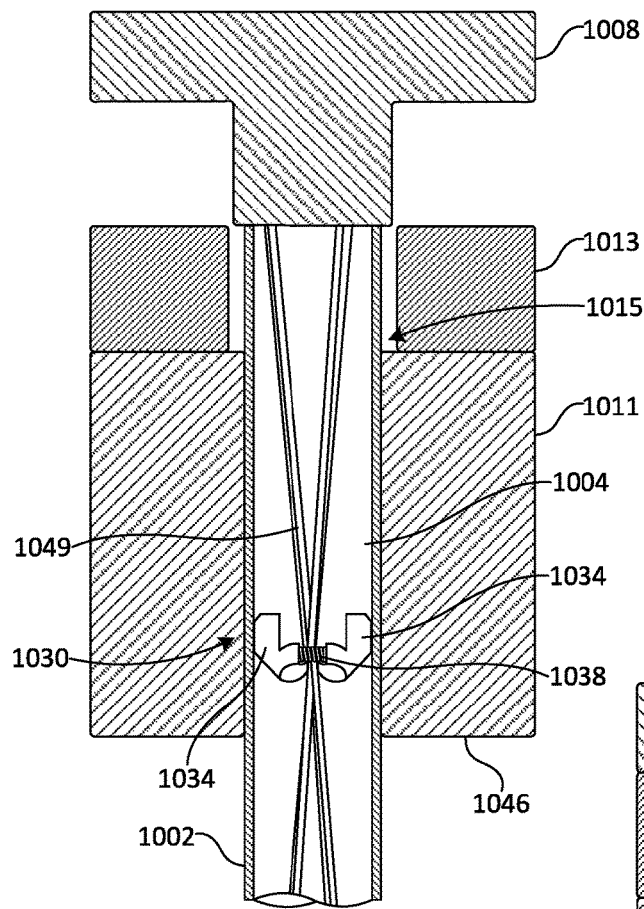
FIGS. 13-16 show diagrams illustrating how retention tabs of a first latching mechanism configuration are deployed upon passage through a mounting fixture, optionally with cable engagement when the retention tabs are in a deployed state or a non-deployed state.
Figure 14:
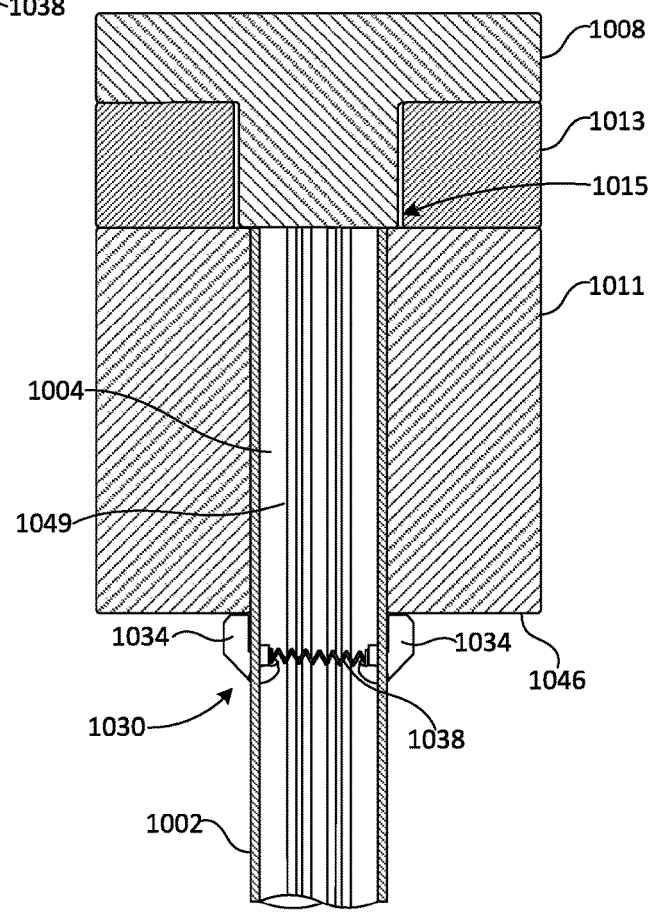
Figure 15:
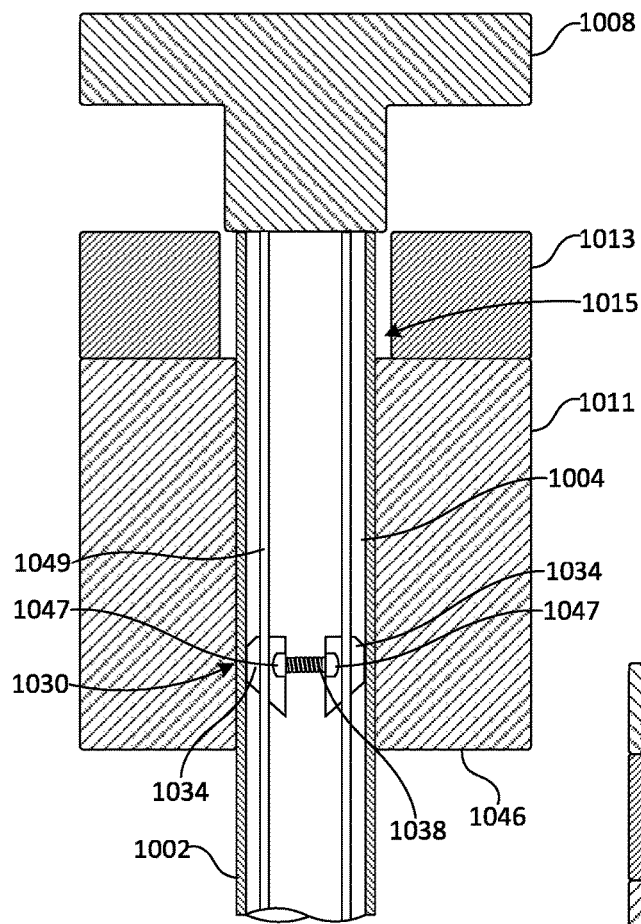
Figure 16:
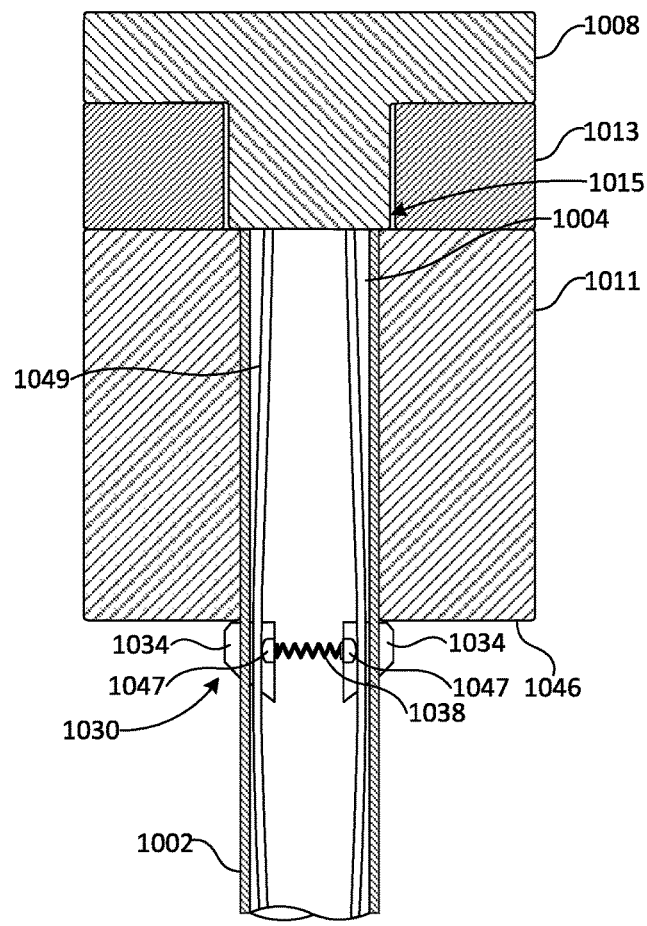

FIGS. 13-16 show diagrams illustrating how retention tabs 1034 deploy upon passing latching mechanism 1030 through channel 1015 of mounting fixture 1011. As shown in FIGS. 13 and 15, retention tabs 1034 are stowed or partially stowed within lumen 1004 when latching mechanism 1030 is located within channel 1015. In particular, engagement between retention tabs 1034 and the perimeter (inner) walls of channel 1015 may force retention tabs 1034 to the retracted state, thereby allowing elongate shaft 1002 to pass through mounting fixture 1011. Once latching mechanism 1030 clears mounting fixture 1011 (i.e., exits channel 1015), as shown in FIGS. 14 and 16, retention tabs 1034 may deploy to the deployed state at the urging of the biasing force, at which point retention tabs 1034 can engage exterior surface 1046, such as on the underside of mounting fixture 1011. After retention tabs 1034 have been deployed and engage exterior surface 1046, elongate shaft 1002 may not be withdrawn from mounting fixture 1011 without first moving retention tabs 1034 back to the stowed position. Although exterior surface 1046 may be on the underside of mounting fixture 1011 according to some embodiments, it is to be appreciated that the position of exterior surface 1046 may vary with the tool orientation. As such, the term "underside" is not limited to locations on the bottom of mounting fixture 1011.

As shown in FIG. 13, when retention tabs 1034 are at least partially retracted, a component of retention tabs 1034 or biasing members 1038 may engage cables 1049 within elongate shaft 1002. Engagement of cables 1049 when retention tabs 1034 are at least partially retracted may preclude unwanted articulation of an end effector when removing the surgical tool from mounting fixture 1011. As shown in FIG. 14, disengagement of cables 1049 occurs when retention tabs 1034 are deployed in the depicted configuration of latching mechanism 1030.

In alternative configurations of latching mechanism 1030, a component of retention tabs 1034 or biasing members 1038 may engage cables 1049 within elongate shaft 1002 when retention tabs 1034 are deployed. Such an alternative configuration of latching mechanism 1030 is shown in FIGS. 15 and 16. The alternative configuration of latching mechanism 1030 depicted in FIGS. 15 and 16 differs primarily in how engagement of cables 1049 occurs, and elements having similar function are not described again in detail in the interest of brevity. In brief, internal posts 1047 upon retention tabs 1034 engage cables 1049 during tab deployment to affect cable tensioning. Engagement of cables 1049 when retention tabs 1034 are deployed may provide advantageous tensioning effects during use that may allow more accurate articulation of an end effector to be realized. As shown in FIG. 15, disengagement of cables 1049 from internal posts 1047 occurs when retention tabs 1034 are at least partially retracted.

In still other alternative configurations of latching mechanism 1030, engagement of cables 1049 need not necessarily occur at all when retention tabs 1034 are either deployed or retracted, such as shown in FIGS. 10 and 11.

Figure 17:
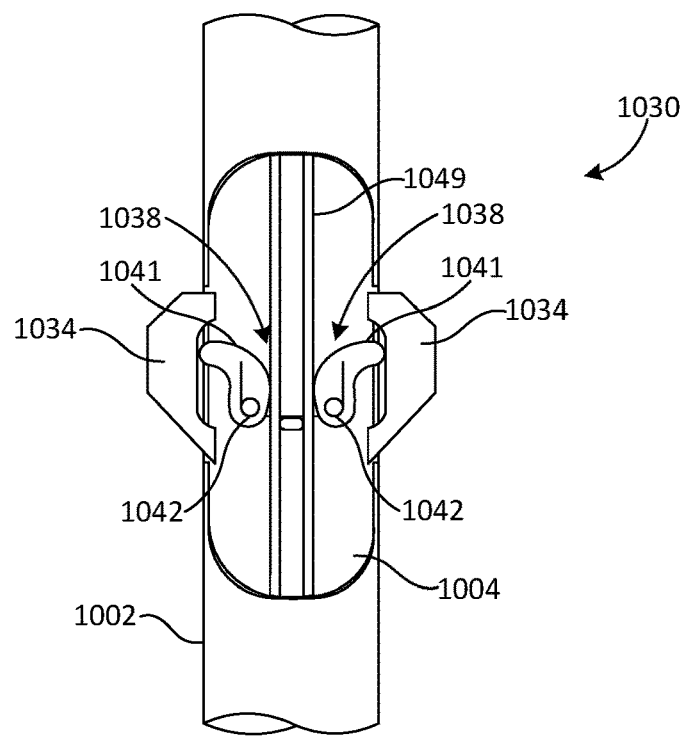
FIGS. 17 and 18 show diagrams illustrating a first latching mechanism configuration in which a biasing force is supplied by spring-loaded cams.
Figure 18:
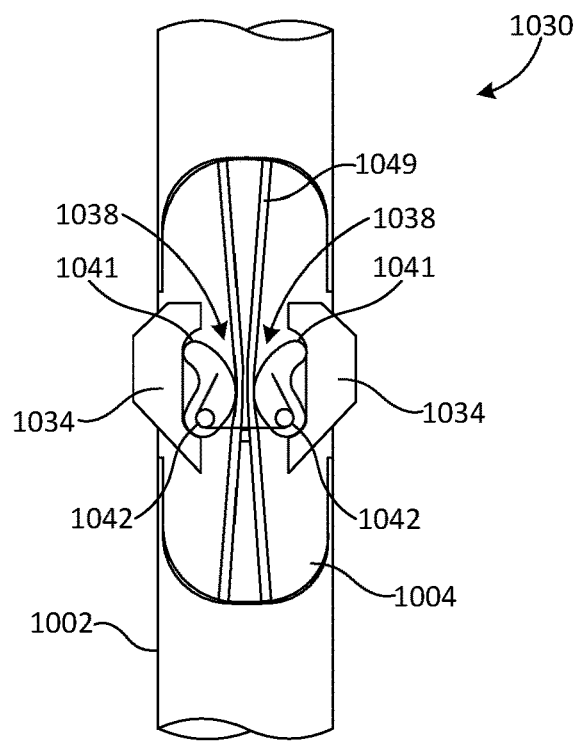

An alternative configuration of latching mechanism 1030 may include embodiments in which biasing members 1038 are spring-loaded cams, as shown in FIGS. 17 and 18. Specifically, in FIGS. 17 and 18, latching mechanism 1030 includes retention tabs 1034 that are configured to interact with cams 1041. Cams 1041 are configured to pivot (rotate) under increasing force supplied by torsion springs 1042. Torsion springs 1042 may be operably connected to each other, as depicted, or each torsion spring 1042 may be configured to supply a biasing force independently to each cam 1041. Operable connection of torsion springs 1042 to each other may aid in balancing the force applied by latching mechanism 1030 and promote substantially equal movement of retention tabs 1034 or substantially equal tensioning of cables 1049.

In FIG. 17, retention tabs 1034 are outwardly biased to the deployed state with torsion springs 1042 acting on cams 1041 and supplying an outward radial force. In contrast, in FIG. 18, application of a sufficient inward force upon retention tabs 1034 may overcome the biasing force, thereby rotating cams 1041 and allowing retention tabs 1034 to become at least partially stowed within lumen 1004. When retention tabs 1034 are at least partially retracted, as in FIG. 18, cams 1041 may engage cables 1049 within lumen 1004, as depicted, or cable engagement may not occur in other embodiments. In still other alternative configurations that are not depicted herein in the interest of brevity, cams 1041 may engage cables 1049 when retention tabs 1034 are deployed, in a manner similar to that shown in FIGS. 15 and 16.

Figure 19:
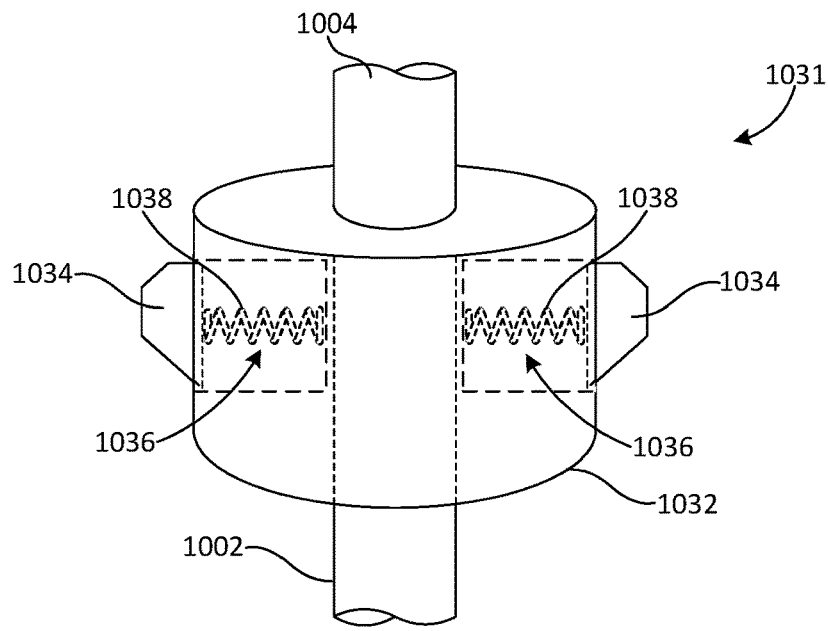
FIGS. 19 and 20 show diagrams illustrating further details of a second latching mechanism configuration, in which retention tabs are in a deployed state and a non-deployed state, respectively.
Figure 20:
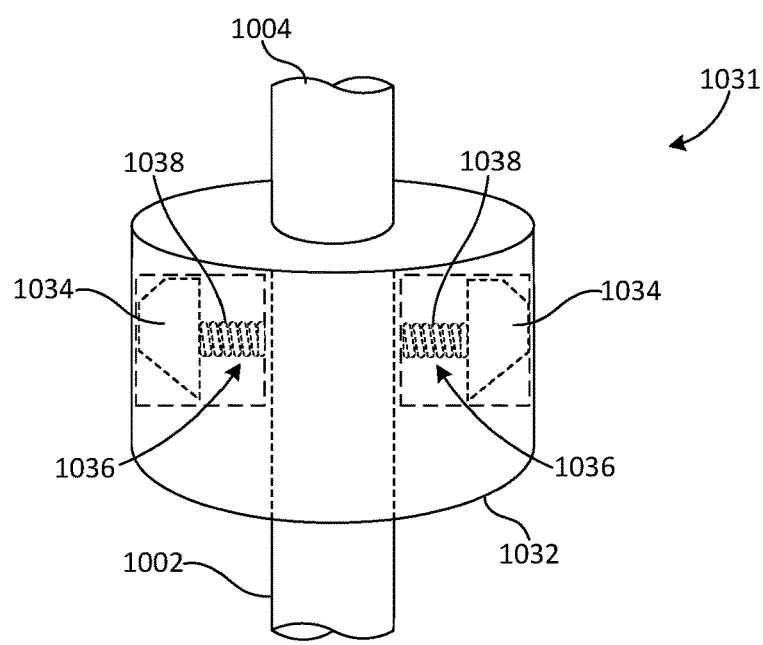

FIGS. 19 and 20 show diagrams illustrating further details of latching mechanism 1031, in which retention tabs 1034 are in a deployed state and a retracted (stowed) state, respectively. As discussed above, latching mechanism 1031 includes latch body 1032 that is operably coupled to the exterior of elongate shaft 1002. Latch body 1032 includes pockets 1036, from which retention tabs 1034 may deploy radially at the urging of a biasing force supplied by biasing member 1038, such as the depicted compression spring. As with latching mechanism 1030, other structures capable of supplying a biasing force may also be employed in latching mechanism 1031, and the depicted compression spring should not be considered limiting. For example, in alternative embodiments, a cam-supplied biasing force, such as that shown in FIGS. 17 and 18, or a hydraulic or pneumatic piston may be used. Other structures suitable for applying a biasing force also include those listed above.

Likewise, the outer diameter of latch body 1032 may be sized for transit through channel 1015 of mounting fixture 1011, as described above in more detail for latching mechanism 1030. More particularly, latch body 1032 may be sized such that retention tabs 1034 engage the perimeter walls of channel 1015 to promote at least partial retraction of retention tabs 1034 and facilitate passage through mounting fixture 1011. In the interest of brevity, further details of the deployment and engagement of retention tabs 1034 in latching mechanism 1031 are not provided herein, but it is to be understood that such details bear significant similarity to those associated with latching mechanism 1030, as can be appreciated by one having ordinary skill in the art. Additionally, it is to be recognized that latch body 1032 may be further configured, according to some embodiments, to provide for cable engagement when retention tabs 1034 are stowed or retracted.

When retention tabs 1034 are at least partially stowed within lumen 1004, as shown in FIGS. 13 and 18, retention tabs 1034 or a component thereof may engage one or more cables 1049 passing through lumen 1004 and extending to an end effector. Alternately, engagement of cables 1049 may occur when retention tabs 1034 are deployed, as shown in FIG. 16. Similar cable engagement may also occur for various configurations of latching mechanism 1031, according to some embodiments. In some embodiments, such engagement may occur with sufficient force to lock cables 1049 against further longitudinal movement. Cable locking may be desirable to preclude unwanted movement of the end effector, for example, such as when removing robotic surgical tool 1000 from mounting fixture 1011. In other embodiments, engagement of cables 1049 may provide advantageous tensioning effects without locking cables 1049 into a fixed position.

In some embodiments, one or more components of the biasing members may comprise a compliant material to increase the frictional force during cable engagement. Suitable compliant materials may include polymers such as silicone rubber, for example. In illustrative embodiments, the compliant material may be coupled to a biasing member in a suitable manner to move under the urging of an applied biasing force.

When deployed and engaged against exterior surface 1046 on the underside of mounting fixture 1011, retention tabs 1034 aid in precluding an accidental tool release. When disengagement of housing 1008 from mounting fixture 1011 is subsequently desired, retention tabs 1034 can be squeezed inwardly to overcome the outward radial biasing force supplied by biasing members 1038. In some embodiments, a user can inwardly retract retention tabs 1034 simply by squeezing with one's fingers. In alternative embodiments, a removal tool can be used to engage retention tabs 1034 in order to promote retraction thereof. Once retention tabs 1034 have been stowed or retracted, tool removal from mounting fixture 1011 may take place.

When used, a removal tool used for retracting retention tabs 1034 may be operated manually or with a robotic manipulator. In addition, the removal tool may be operably coupled to elongate shaft 1002 and movable to a position suitable for engaging retention tabs 1034, according to some embodiments, or the removal tool may be placed upon elongate shaft 1002 only when tool decoupling is desired, according to other embodiments. Placement of the removal tool upon elongate shaft 1002 may take place before or after conducting a surgical procedure. In still other embodiments, a retention tool need not engage elongate shaft 1002 at all when affecting removal of the robotic surgical tool.

Regardless of how removal tool positioning takes place, the removal tool may be positioned adjacent to retention tabs 1034 and undergo subsequent engagement therewith once tool removal is desired. In some embodiments, the removal tool may be positioned after withdrawing the robotic surgical tool from a patient upon completion of a surgical procedure. In such embodiments, the removal tool may pass over the end effector and a distal end of elongate shaft 1002, particularly when the removal tool circumferentially surrounds elongate shaft 1002. Alternately, the removal tool may be assembled in-place around elongate shaft 1002 (e.g., by operably connecting two halves of a toroid-shaped or other closed geometric shape) and then engaging retention tabs 1034. In still other embodiments, the removal tool need not necessarily surround elongate shaft 1002 in order for retraction of retention tabs 1034 to take place. For example, some configurations of a suitable removal tool may have a cutout allowing for the removal tool to be placed around elongate shaft 1002 and positioned for retracting retention tabs 1034, but without passing over the end effector.

In some embodiments, the removal tool may comprise a chamfered surface that is shaped to engage retention tabs 1034 and push them inward. Other suitable configurations for a removal tool may include structures that may be ratcheted, pivoted, constricted (e.g., with a belt or hydraulic piston), or inflated, for example, to engage retention tabs 1034 and provide a sufficient force to push them inward.

Figure 21:
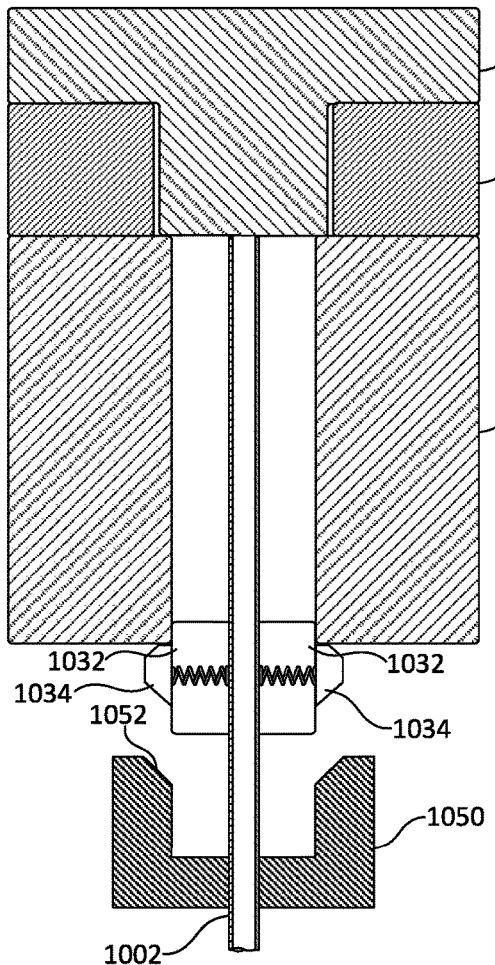
FIGS. 21 and 22 show diagrams illustrating how a removal tool with a chamfered surface may facilitate retraction of retention tabs in a latching mechanism.
Figure 22:
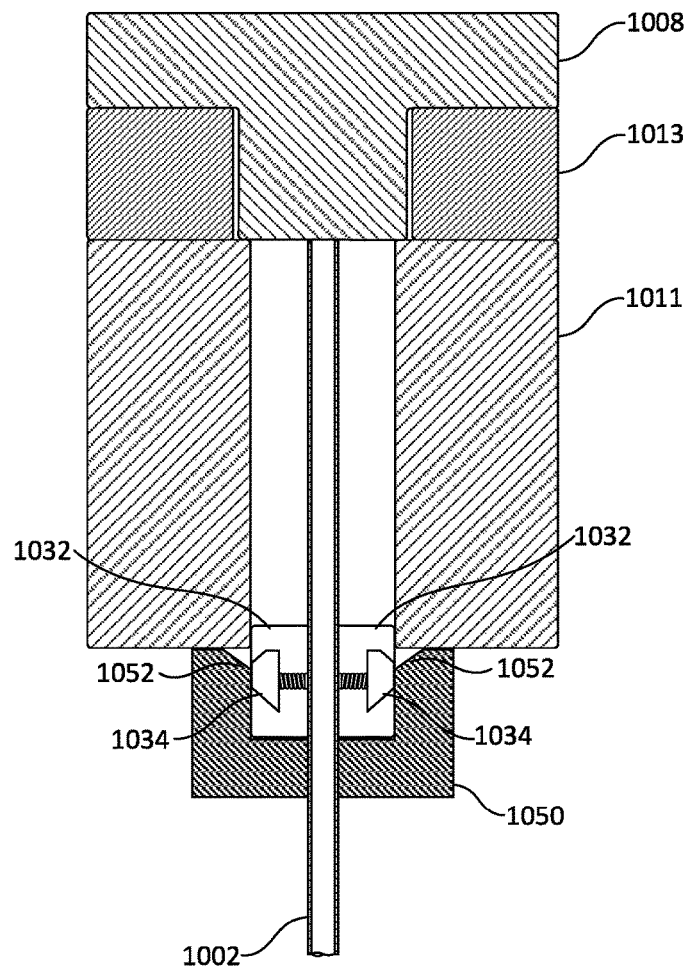

FIGS. 21 and 22 show diagrams illustrating how removal tool 1050 with chamfered surfaces 1052 may facilitate retraction of retention tabs 1034. As shown in FIG. 21, removal tool 1050 may be positioned around elongate shaft 1002 below retention tabs 1034, which are engaged with the underside of mounting fixture 1011. Once it is desired to retract retention tabs 1034, removal tool 1050 may be raised and/or the mounting fixture 1011 may be lowered such that chamfered surfaces 1052 engage retention tabs 1034, as shown in FIG. 22. Engagement between chamfered surfaces 1052 and retention tabs 1034 may overcome the biasing force supplied by biasing members 1032 and push retention tabs 1034 inwardly, thereby allowing the robotic surgical tool to be withdrawn through mounting fixture 1011, as discussed in more detail above. Although FIGS. 21 and 22 have shown removal tool 1050 engaging retention tabs 1034 within a latching mechanism configuration similar to that of latching mechanism 1031, it is to be appreciated that similar removal concepts may apply for any of the latching mechanisms disclosed herein. More specifically, a latching mechanism similar to that of latching mechanism 1030 may be manipulated similarly to the latching mechanism shown in FIGS. 21 and 22 without departing from the spirit and scope of the present disclosure.

When used, removal tool 1050 may be positioned around elongate shaft 1002 prior to performing a surgical procedure, according to some embodiments. In other embodiments, positioning of removal tool 1050 around elongate shaft 1002 may be delayed until removal of the robotic surgical tool is desired. For example, in some embodiments, removal tool 1050 may be positioned around elongate shaft 1002 after the robotic surgical tool has completed its intended function, either before or after being removed from the patient's body.

When being positioned after tool removal from the patient's body, removal tool 1050 may pass over the end effector before becoming situated on or around elongate shaft 1002. In still other alternative embodiments, removal tool 1050 need not necessarily be disposed upon or around elongate shaft 1002 at all. For example, in some embodiments, the robotic surgical tool may be moved to a separate location to affect engagement of retention tabs 1034 with removal tool 1050.

In addition to those described above and shown in FIGS. 21 and 22, suitable configurations for removal tool 1050 may also include those that are configured to engage retention tabs 1034 without having to pass over the end effector of the robotic surgical tool. Suitable configurations may include U-shaped or similarly shaped tools having a cutout or recess, and hinged or unhinged removal having two or more pieces that are configured to work cooperatively together to provide appropriate surfaces for engaging retention tabs 1034 to affect tool removal. Any of these removal tools 1050 may likewise be positioned and operated manually or with a robotic manipulator.

Embodiments disclosed herein include: A. Robotic surgical tools. The robotic surgical tools comprise: a tool housing; an elongate shaft coupled to and extending from the tool housing, the elongate shaft further defining a lumen that extends between a proximal end and a distal end of the elongate shaft; and a latching mechanism arranged on the elongate shaft and comprising one or more retention tabs that are biased radially outward with one or more biasing members; wherein the one or more retention tabs are movable between a deployed state, in which the one or more retention tabs extend radially outward from the elongate shaft and are positioned to engage an exterior surface of a mounting fixture of a robotic manipulator, and a retracted state, in which the one or more retention tabs are urged radially inward and are positioned to disengage the exterior surface of the mounting fixture.

B. Robotic surgical systems. The robotic surgical systems comprise: a robotic manipulator comprising a mounting fixture; a robotic surgical tool removably coupled to the mounting fixture, the robotic surgical tool comprising: a tool housing; an elongate shaft coupled to and extending from the tool housing, the elongate shaft further defining a lumen that extends between a proximal end and a distal end of the elongate shaft; and a latching mechanism arranged on the elongate shaft and comprising one or more retention tabs that are biased radially outward with one or more biasing members; wherein the one or more retention tabs are movable between a deployed state, in which the one or more retention tabs extend radially outward from the elongate shaft and are positioned to engage an exterior surface of a mounting fixture of the robotic manipulator, and a retracted state, in which the one or more retention tabs are urged radially inward and are positioned to disengage the exterior surface of the mounting fixture.

C. Methods for situating a robotic surgical tool in a mounting fixture. The methods comprise: inserting an elongate shaft of a robotic surgical tool through a channel defined in a mounting fixture of a robotic manipulator, the robotic surgical tool comprising a latching mechanism arranged on the elongate shaft, a tool housing coupled to a proximal end of the elongate shaft, and an end effector coupled to a distal end of the elongate shaft, a lumen being defined in the elongate shaft and extending between the proximal end and the distal end; passing the latching mechanism through the channel while inserting the elongate shaft; deploying one or more retention tabs radially outward from the latching mechanism once the latching mechanism passes through the channel; wherein the one or more retention tabs are biased radially outward with one or more biasing members; and engaging the one or more retention tabs against an exterior surface of the mounting fixture once deployed.

Each of embodiments A, B, and C may have one or more of the following additional elements in any combination Element 1: wherein the one or more biasing members are located within the lumen.

Element 2: wherein the one or more retention tabs comprise a first retention tab and a second retention tab, and the one or more biasing members extend between the first retention tab and the second retention tab.

Element 3: wherein the latching mechanism comprises a latch body that is operably coupled to an exterior of the elongate shaft, the latch body comprising one or more pockets extending to an outer radial surface of the latch body, and each pocket housing a biasing member.

Element 4: wherein the one or more biasing members comprise one or more compression springs.

Element 5: wherein the one or more biasing members comprise one or more spring-loaded cams.

Element 6: wherein the latching mechanism is configured to retract the one or more retention tabs when passing at least a portion of the elongate shaft through a channel in the mounting fixture, the portion of the elongate shaft containing the latching mechanism.

Element 7: wherein the robotic surgical tool is configured to engage the latching mechanism with a removal tool, the removal tool being adapted to transition the one or more retention tabs to the retracted state.

Element 8: wherein the robotic surgical tool further comprises: a plurality of elongate members extending through the lumen and operably engaging an end effector coupled to the distal end of the elongate shaft; wherein a component of the one or more biasing members or the one or more retention tabs is configured to engage one or more of the elongate members when the one or more retention tabs are in the retracted state.

Element 9: wherein the robotic surgical tool further comprises: a plurality of elongate members extending through the lumen and operably engaging an end effector coupled to the distal end of the elongate shaft; wherein a component of the one or more biasing members or the one or more retention tabs is configured to engage one or more of the elongate members when the one or more retention tabs are in the deployed state.

Element 10: wherein the one or more biasing members comprise one or more compression springs or spring-loaded cams.

Element 11: wherein the method further comprises: applying an inward radial force to the one or more retention tabs, the inward radial force being sufficient to overcome an outward radial biasing force supplied by the one or more biasing members and thereby retracting the one or more retention tabs; and withdrawing the robotic surgical tool from the mounting fixture.

Element 12: wherein the method further comprises: engaging one or more elongate members extending within the lumen with a component of the one or more biasing members or the one or more retention tabs when the one or more retention tabs are retracted.

Element 13: wherein the method further comprises: engaging one or more elongate members extending within the lumen with a component of the one or more biasing members or the one or more retention tabs when the one or more retention tabs are deployed.

By way of non-limiting example, exemplary combinations applicable to A, B, C include: The robotic surgical tool of A, the robotic surgical system of B, or the method of C in further combination with elements: 1 and 2; 2 and 3; 2 and 4; 2 and 5; 1 and 7; 2 and 7; 3 and 7; 4 and 7; 1 and 8; 1 and 9; 3 and 4; 3 and 5; 1 and 6; 2 and 6; 3 and 6; 7 and 8; and 7 and 9. The method of C in further combination with elements 11 and 12; and 11 and 13, optionally in further combination with elements 1-7, or elements 1 and 2; 2 and 3; 2 and 4; 2 and 5; 1 and 7; 2 and 7; 3 and 7; 4 and 7; 3 and 4; 3 and 5; 1 and 6; 2 and 6; and 3 and 6.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A robotic surgical system comprising:
   a robotic manipulator that includes a mounting fixture defining a longitudinal channel; and
   a surgical tool removably coupleable to the mounting fixture and including:
      a tool housing mateable with the mounting fixture;
      an elongate shaft extending from the tool housing and receivable within the channel; and
      a latching mechanism provided on the elongate shaft and comprising one or more retention tabs biased radially outward with one or more biasing members,
   wherein the one or more retention tabs are movable between a deployed state, where the one or more retention tabs protrude radially outward through a corresponding one or more slots to engage the mounting fixture, and a retracted state, where the one or more retention tabs are urged radially inward through the one or more slots to disengage the mounting fixture, and
   wherein the one or more retention tabs engage an exterior surface of the mounting fixture when moved to the deployed state.

2. The robotic surgical system of claim 1, wherein the one or more biasing members are located within a lumen and the one or more slots are defined in the elongate shaft.

3. The robotic surgical system of claim 1, wherein the latching mechanism comprises a latch body coupled to an exterior of the elongate shaft, and wherein the one or more biasing members are arranged within the latch body.

4. The robotic surgical system of claim 3, wherein the one or more slots are defined in the latch body.

5. The robotic surgical system of claim 1, wherein the longitudinal channel is open on one longitudinal side of the mounting fixture.

6. The robotic surgical system of claim 1, wherein the exterior surface of the mounting fixture is an underside of the mounting fixture at a bottom of the channel.

7. The robotic surgical system of claim 1, further comprising:
   a lumen defined by the elongate shaft and extending between proximal and distal ends of the elongate shaft; and a plurality of elongate members extending through the lumen from the tool housing to an end effector arranged at the distal end of the elongate shaft,
wherein the mounting fixture houses one or more motors operable to actuate a corresponding one or more mechanisms housed within the tool housing to manipulate the plurality of elongate members and thereby actuate the end effector.

* * * * *